US008058489B2

(12) United States Patent
Rao et al.

(10) Patent No.: US 8,058,489 B2
(45) Date of Patent: Nov. 15, 2011

(54) PROCESSES FOR PRODUCING PENTAFLUOROPROPENES AND AZEOTROPES COMPRISING HF AND CERTAIN HALOPROPENES OF THE FORMULA $C_3CL_2F_4$, $C_3CLF_5$, OR $C_3HF_5$

(75) Inventors: Velliyur Nott Mallikarjuna Rao, Wilmington, DE (US); Allen Capron Sievert, Elkton, MD (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 353 days.

(21) Appl. No.: 12/444,598

(22) PCT Filed: Nov. 15, 2007

(86) PCT No.: PCT/US2007/024058
§ 371 (c)(1),
(2), (4) Date: Apr. 7, 2009

(87) PCT Pub. No.: WO2008/060612
PCT Pub. Date: May 22, 2008

(65) Prior Publication Data
US 2010/0051852 A1    Mar. 4, 2010

Related U.S. Application Data

(60) Provisional application No. 60/859,186, filed on Nov. 15, 2006.

(51) Int. Cl.
C07C 17/10 (2006.01)
C07C 17/00 (2006.01)
(52) U.S. Cl. .......................... 570/176; 570/156; 570/181
(58) Field of Classification Search .................. 570/156, 570/176, 181, 204
See application file for complete search history.

(56) References Cited

U.S. PATENT DOCUMENTS

| 2,856,435 | A | 10/1958 | Lo et al. |
| 3,081,358 | A | 3/1963 | Agahigian et al. |
| 5,396,000 | A | 3/1995 | Nappa et al. |
| 2006/0106263 | A1 | 5/2006 | Miller et al. |

FOREIGN PATENT DOCUMENTS

| CA | 663257 | 5/1963 |
| DE | 1139831 | 11/1962 |
| JP | 8-193039 | 7/1996 |
| WO | 20040037752 | 5/2004 |
| WO | 20050058489 | 6/2005 |
| WO | 2008054780 | 5/2008 |
| WO | 2008060614 | 5/2008 |
| WO | 2008060616 | 5/2008 |

OTHER PUBLICATIONS

U.S. Appl. No. 12/442,952.
U.S. Appl. No. 12/514,348.
U.S. Appl. No. 12/444,526.
Database WPI Week 199640 Thomson Scientific, London GB; AN 1996-397213 XP002492282 & JP 08193039 A (Daikin Kogyo KK) Jul. 30, 1996 Paragraph 52-80 Abstract.
William T. Miller et al.: "Preferential Replacement Reactions of Highly Fluorinated Alkyl Halides. I. Preparation of Certain Fluorinated Allyl Iodides" Journal of the American Chemical Society, vol. 79, 1957, p. 4164-4169, XP002492280 Table I; No. IIa, IIb, IV p. 4164, Last Paragraph.
Paleta Oldrich et al: "Synthesis of Perfluoroallyl Chloride and Some Chlorofluoropropenes" Bulletin De La Societe Chimique De France, Societe Francaise De Chimie. Paris, No. 6, Jan. 1, 1986, p. 920-924, XP009088473 ISSN:0037-8968 Table I, 8a.
Arnold H. Fainberg et al.: "Preferential Replacement Reactions of Highly Fluorinated Alkyl Halides. II. Some Reactions of Fluorinated Allyl Iodides" Journal of the American Chemical Society, vol. 79, 1957, pp. 4170-4174, XP002492281 Table I, VIII.

Primary Examiner — Jafar Parsa

(57) ABSTRACT

A process is disclosed for making $CF_3CF{=}CHF$ or mixtures thereof with $CF_2{=}CFCHF_2$. The process involves (i) contacting $CHCl_2CF_2CF_3$, and optionally $CHClFCF_2CClF_2$, in a reaction zone in the presence of a catalytically effective amount of dehydrofluorination catalyst to produce $CCl_2{=}CFCF_3$, and, if $CHClFCF_2CClF_2$ is present, $CClF{=}CFCClF_2$; (ii) contacting $CCl_2{=}CFCF_3$ and $CClF{=}CFCClF_2$, if any, formed in (i) with hydrogen fluoride (HF) in a reaction zone, optionally in the presence of a fluorination catalyst, to produce $CClF{=}CFCF_3$, and if $CClF{=}CFCClF_2$ is present, $CF_2{=}CFCClF_2$; (iii) contacting $CClF{=}CFCF_3$ and $CF_2{=}CFCClF_2$, if any, formed in (ii) in a reaction zone with $H_2$ in the presence of a catalyst comprising a catalytically effective amount of palladium supported on a support of chromium oxide, fluorinated chromium oxide, chromium fluoride, aluminum oxide, aluminum fluoride, and/or fluorinated alumina to produce a product mixture comprising $CF_3CF{=}CHF$, and if $CF_2{=}CFCClF_2$ is present, $CF_2{=}CFCHF_2$; and (iv) recovering $CF_3CF{=}CHF$, or a mixture thereof with $CF_2{=}CFCHF_2$, from the product mixture formed in (iii); and optionally (v) separating at least a portion of any $CF_3CF{=}CHF$ in the product mixture formed in (iii) from the $CF_2{=}CFCHF_2$ in the product mixture formed in (iii).
Also disclosed are azeotropic compositions involving $CCl_2{=}CFCF_3$ and HF; involving $CCl_2{=}CFCF_3$, $CClF{=}CFCClF_2$ and HF; involving $CClF{=}CFCF_3$ and HF; involving $CClF{=}CFCF_3$, $CF_2{=}CFCClF_2$ and HF; or involving $CF_2{=}CFCHF_2$ and HF.

12 Claims, No Drawings

PROCESSES FOR PRODUCING PENTAFLUOROPROPENES AND AZEOTROPES COMPRISING HF AND CERTAIN HALOPROPENES OF THE FORMULA $C_3CL_2F_4$, $C_3CLF_5$, OR $C_3HF_5$

FIELD OF THE INVENTION

The present invention relates to processes that involve the production of halogenated hydrocarbon products comprising 1,2,3,3,3-pentafluoropropene.

BACKGROUND OF THE INVENTION

As a result of the Montreal Protocol phasing out ozone depleting chlorofluorocarbons (CFCs) and hydrochlorofluorocarbons (HCFCs), industry has been working for the past few decades to find replacement refrigerants. The solution for most refrigerant producers has been the commercialization of hydrofluorocarbon (HFC) refrigerants. The new hydrofluorocarbon refrigerants, HFC-134a ($CF_3CH_2F$) being the most widely used at this time, have zero ozone depletion potential and thus are not affected by the current regulatory phase out as a result of the Montreal Protocol. The production of other hydrofluorocarbons for use in applications such as solvents, blowing agents, cleaning agents, aerosol propellants, heat transfer media, dielectrics, fire extinguishants and power cycle working fluids has also been the subject of considerable interest.

There is considerable interest in developing new refrigerants with reduced global warming potential, as well as zero ozone depletion potential, for the mobile air-conditioning market, and in other refrigeration applications.

HFC-1225ye ($CF_3CF=CHF$), having zero ozone depletion and a low global warming potential, has been identified as a potential refrigerant. U.S. Pat. No. 5,396,000 discloses a process for producing HFC-1225ye by dehydrofluorination of $CF_3CFHCF_2H$ (HFC-236ea). There is a need for new manufacturing processes for the production of HFC-1225ye.

1,1,2,3,3-Pentafluoro-1-propene ($CF_2=CFCHF_2$, HFC-1225yc) is useful as a monomer for the manufacture of fluoropolymers.

SUMMARY OF THE INVENTION

The present invention provides a process for making $CF_3CF=CHF$ or mixtures thereof with $CF_2=CFCHF_2$. The process comprises (i) contacting $CHCl_2CF_2CF_3$ (HCFC-225ca), and optionally $CHClFCF_2CClF_2$ (HCFC-225cb), in a reaction zone in the presence of a catalytically effective amount of dehydrofluorination catalyst to produce $CCl_2=CFCF_3$ (CFC-1214ya), and, if $CHClFCF_2CClF_2$ (HCFC-225cb) is present, E- and/or Z—$CClF=CFCClF_2$ (CFC-1214yb); (ii) contacting $CCl_2=CFCF_3$ (CFC-1214ya) and E- and/or Z—$CClF=CFCClF_2$ (CFC-1214yb), if any, formed in (i) with hydrogen fluoride (HF) in a reaction zone, optionally in the presence of a fluorination catalyst, to produce E- and/or Z—$CClF=CFCF_3$ (CFC-1215yb), and if E- and/or Z—$CClF=CFCClF_2$ (CFC-1214yb) is present, $CF_2=CFCClF_2$ (CFC-1215yc); (iii) contacting E- and/or Z—$CClF=CFCF_3$ (CFC-1215yb) and $CF_2=CFCClF_2$ (CFC-1215yc), if any, formed in (ii) in a reaction zone with hydrogen ($H_2$) in the presence of a catalyst comprising a catalytically effective amount of palladium supported on a support selected from the group consisting of chromium oxide, fluorinated chromium oxide, chromium fluoride, aluminum oxide, aluminum fluoride, fluorinated alumina, and mixtures thereof to produce a product mixture comprising E- and/or Z—$CF_3CF=CHF$ (HFC-1225ye), and if $CF_2=CFCClF_2$ (CFC-1215yc) is present, $CF_2=CFCHF_2$ (HFC-1225yc); and (iv) recovering E- and/or Z—$CF_3CF=CHF$ (HFC-1225ye), or a mixture thereof with $CF_2=CFCHF_2$ (HFC-1225yc), from the product mixture formed in (iii); and optionally (v) separating at least a portion of any E- and/or Z—$CF_3CF=CHF$ (HFC-1225ye) in the product mixture formed in (iii) from the $CF_2=CFCHF_2$ (HFC-1225yc) in the product mixture formed in (iii).

The present invention also provides a composition comprising (a) $CCl_2=CFCF_3$ and (b) HF; wherein the HF is present in an effective amount to form an azeotropic combination with $CCl_2=CFCF_3$.

The present invention also provides a composition comprising (a) a mixture of $CCl_2=CFCF_3$ and E- and/or Z—$CClF=CFCClF_2$ and (b) HF; wherein the HF is present in an effective amount to form an azeotropic combination with said mixture of $CCl_2=CFCF_3$ and E- and/or Z—$CClF=CFCClF_2$.

The present invention also provides a composition comprising (a) E- and/or Z—$CClF=CFCF_3$ and (b) HF; wherein the HF is present in an effective amount to form an azeotropic combination with the E- and/or Z—$CClF=CFCF_3$.

The present invention also provides a composition comprising (a) a mixture of E- and/or Z—$CClF=CFCF_3$ and $CF_2=CFCClF_2$ and (b) HF; wherein the HF is present in an effective amount to form an azeotropic combination with said mixture of E- and/or Z—$CClF=CFCF_3$ and $CF_2=CFCClF_2$.

The present invention also provides a composition comprising (a) $CF_2=CFCHF_2$ and (b) HF; wherein the HF is present in an effective amount to form an azeotropic combination with $CF_2=CFCHF_2$.

DETAILED DESCRIPTION

The present invention provides a process for making HFC-1225ye or mixtures thereof with HFC-1225yc employing a multi-step process. As noted above, the multi-step process involves CFC-1215yb and in some embodiments, CFC-1215yc, as intermediate reaction products. HFC-1225ye, CFC-1215yb, and CFC-1214yb may exist as one of two configurational isomers, E or Z. HFC-1225ye as used herein refers to the isomers, E-HFC-1225ye (CAS Reg No. [5595-10-8]) or Z—HFC-1225ye (CAS Reg. No. [5528-43-8]), as well as any combinations or mixtures of such isomers. CFC-1215yb as used herein refers to the isomers, E-CFC-1215yb (CAS Reg. No. [14003-62-4]) or Z—CFC-1215yb (CAS Reg. No. [14003-57-7]), as well as any combinations or mixtures of such isomers. CFC-1214yb as used herein refers to the isomers, E-CFC-1214yb (CAS Reg. No. [111512-50-6]) or Z—CFC-1214yb (CAS Reg. No. [111512-61-9]), as well as any combinations or mixtures of such isomers.

In the first step of the process, HCFC-225ca, and optionally HCFC-225cb, is dehydrofluorinated over a suitable catalyst for a time sufficient to convert at least a portion of HCFC-225 to CFC-1214. Dehydrofluorination of HCFC-225ca produces CFC-1214ya. If HCFC-225cb is present during the contacting step, the CFC-1214 produced comprises CFC-1214yb.

Of note are embodiments wherein the $C_3HCl_2F_5$ component (that is, the total of HCFC-225ca and HCFC-225cb) subjected to dehydrofluorination is primarily HCFC-225ca. Of particular note are embodiments wherein the $C_3HCl_2F_5$ subjected to dehydrofluorination is essentially free of HCFC-225cb.

Mixtures of HCFC-225ca and HCFC-225cb can be prepared by the reaction of dichlorofluoromethane (HCFC-21) with tetrafluoroethylene (TFE) in the presence of aluminum chloride as reported by Paleta, et. al. in Collections of Czechoslovakia Chemical Communications, Vol. 36, pages 1867 to 1875 (1971) or by the reaction of dichlorofluoromethane (HCFC-21) with tetrafluoroethylene (TFE) in the presence of aluminum chlorofluoride as disclosed in U.S. Pat. No. 5,157,171. In particular, $C_3HCl_2F_5$ (i.e., HCFC-225ca and HCFC-225cb) can be produced by reacting $CHCl_2F$ with $CF_2=CF_2$ in a reaction zone in the presence of a catalytically effective amount of an aluminum halide composition having a bulk formula of $AlCl_xBr_yF_{3-x-y}$, wherein the average value of x is 0 to 3, the average value of y is 0 to 3-x, provided that the average values of x and y are not both 0.

HCFC-225ca, free of HCFC-225cb, may be prepared by reacting $CCl_3CF_2CF_3$ (CFC-215cb) with hydrogen as disclosed by Baker in U.S. Pat. No. 5,300,712. CFC-215cb, free of the $CCl_2FCF_2CClF_2$ (CFC-215ca) isomer, may be prepared by reaction of $CCl_3F$ with more than one equivalent of TFE as disclosed in U.S. Provisional Patent Application No. 60/855,541, filed Oct. 31, 2006 (see also PCT/US2007/22993, filed Oct. 31, 2007).

The dehydrofluorination reaction may be conducted in the vapor phase in a reaction zone containing the dehydrofluorination catalyst at temperatures of from about 200° C. to about 500° C. and preferably from about 300° C. to about 450° C. The contact time is typically from about 1 to about 450 seconds, preferably from about 10 to about 120 seconds.

The reaction pressure can be sub-atmospheric, atmospheric or super-atmospheric. Generally, near atmospheric pressures are preferred. However, the dehydrofluorination of $C_3HCl_2F_5$ can be beneficially run under reduced pressure (i.e., pressures less than one atmosphere).

The catalytic dehydrofluorination can optionally be carried out in the presence of an inert gas such as nitrogen, helium or argon. The addition of an inert gas can be used to increase the extent of dehydrofluorination. Of note are processes where the mole ratio of inert gas to $C_3HCl_2F_5$ is from about 5:1 to 1:1. Nitrogen is the preferred inert gas.

Typical dehydrofluorination reaction conditions and dehydrofluorination catalysts are disclosed in U.S. Pat. No. 5,396,000, which is herein incorporated by reference in its entirety. Preferably, the dehydrofluorination catalyst comprises at least one catalyst selected from the group consisting of carbon, aluminum fluoride, fluorided alumina, trivalent chromium oxide, and trivalent chromium chloride, fluoride, or chlorofluoride preferably supported on a support such as carbon, aluminum fluoride, or fluorided alumina.

Other dehydrofluorination catalysts useful for converting $C_3HCl_2F_5$ to CFC-1214ya/yb are described in U.S. Pat. Nos. 6,093,859 and 6,369,284; the teachings of these disclosures are incorporated herein by reference.

The effluent from the dehydrofluorination reactor typically includes HF and CFC-1214ya and one or more compounds selected from CFC-1215yb, $CF_3CHFCCl_2F$ (HCFC-225eb), any unconverted HCFC-225ca, and $C_3HClF_6$ and $C_3HCl_3F_4$ isomers. When HCFC-225cb is present as a starting material, the effluent typically also includes CFC-1214yb, some CFC-1215yc and $CClF_2CHFCClF_2$ (HCFC-225ea), and any unconverted HCFC-225cb.

The CFC-1214ya, and CFC-1214yb if present, may be separated from the product mixture formed in the dehydrofluorination reactor by methods known to the art. Since HF is present in the effluent, if desired, this separation can also include isolation of an azeotrope or near azeotrope composition of CFC-1214ya and HF. If CFC-1214yb is present in the reactor effluent, this separation, if desired, can also include isolation of an azeotrope or near azeotrope composition of a mixture of CFC-1214ya and CFC-1214yb and HF. The ratio of CFC-1214ya to CFC-1214yb, present in the CFC-1214 mixture forming the azeotrope or near azeotrope with HF, can vary depending on the ratio of HCFC-225ca and HCFC-225cb fed and/or converted in the dehydrofluorination reactor. HF-free CFC-1214ya, or HF-free CFC-1214ya/CFC-1214yb mixture, may be obtained using procedures similar to those disclosed in U.S. Patent Application Publication No. 2006/0106263 which is hereby incorporated herein by reference. Unreacted HCFC-225ca (and HCFC-225cb if present in the starting material) can be recycled back to the dehydrofluorination reactor.

In the second step of the process of the invention, CFC-1214 is fluorinated in a reaction zone, optionally in the presence of a fluorination catalyst, for a time sufficient to convert at least a portion of CFC-1214 to a second product mixture comprising CFC-1215. Fluorination of CFC-1214ya produces CFC-1215yb. If CFC-1214yb is present during the fluorination reaction, the second product mixture also comprises CFC-1215yc.

Of note are embodiments wherein the $C_3Cl_2F_4$ component (that is, the total of CFC-1214ya and CFC-1214yb) subjected to fluorination is primarily CFC-1214ya. Of particular note are embodiments wherein the $C_3Cl_2F_4$ subjected to fluorination is essentially free of CFC-1214yb.

The fluorination is preferably conducted in the vapor phase in the presence of a fluorination catalyst. Suitable fluorination catalysts which may be used in the vapor phase reaction of the invention include carbon; graphite; alumina; fluorided alumina; aluminum fluoride; alumina supported on carbon; aluminum fluoride supported on carbon; fluorided alumina supported on carbon; magnesium fluoride supported on aluminum fluoride; metals (including elemental metals, metal oxides, metal halides, and/or other metal salts); metals supported on aluminum fluoride; metals supported on fluorided alumina; metals supported on alumina; and metals supported on carbon; mixtures of metals.

Suitable metals for use as catalysts (optionally supported on alumina, aluminum fluoride, fluorided alumina, or carbon) include chromium, iron, cobalt, nickel, ruthenium, rhodium, palladium, osmium, iridium, platinum, manganese, rhenium, scandium, yttrium, lanthanum, titanium, zirconium, and hafnium, copper, silver, gold, zinc, and/or metals having an atomic number of 58 through 71 (i.e., the lanthanide metals). Preferably when used on a support, the total metal content of the catalyst will be from about 0.1 to about 20 percent by weight based on the total weight of the catalyst; typically from about 0.1 to about 10 percent by weight based on the total weight of the catalyst.

Of note are vapor phase fluorination embodiments wherein the fluorination catalysts include chromium-containing catalysts including chromium(III) oxide ($Cr_2O_3$); $Cr_2O_3$ with other metals such as magnesium halides or zinc halides supported on $Cr_2O_3$; chromium(III) halides supported on carbon; mixtures of chromium and magnesium (including elemental metals, metal oxides, metal halides, and/or other metal salts) optionally supported on graphite; and mixtures of chromium and other metals (including elemental metals, metal oxides, metal halides, and/or other metal salts) optionally supported on graphite, alumina, or aluminum halides such as aluminum fluoride.

Chromium-containing catalysts are well known in the art. They may be prepared by either precipitation methods or impregnation methods as generally described by Satterfield on pages 87-112 in *Heterogeneous Catalysis in Industrial Practice*, 2$^{nd}$ edition (McGraw-Hill, New York, 1991).

Optionally, the metal-containing catalysts described above can be pretreated with HF. This pretreatment can be accomplished, for example, by placing the metal-containing catalyst in a suitable container, and thereafter, passing HF over the metal-containing catalyst. In one embodiment of this invention, such container can be the reactor used to perform the fluorination reaction in this invention. Typically, the pretreatment time is from about 15 to about 300 minutes, and the pretreatment temperature is from about 200° C. to about 450° C.

Suitable temperatures for the vapor-phase fluorination of CFC-1214 are from about 120° C. to about 500° C., preferably from about 200° C. to about 450° C. and most preferably from about 250° C. to about 350° C. Suitable reactor pressures for the fluorination reactor may be from about 1 to about 30 atmospheres. A pressure of about 15 to about 25 atmospheres may be advantageously employed to facilitate separation of HCl from other reaction products, and the suitable reaction time may vary from about 1 to about 120 seconds, preferably from about 5 to about 60 seconds.

The molar ratio of HF to the total amount of CFC-1214 for the vapor-phase fluorination reaction is typically from about the stoichiometric ratio of HF to the total amount of CFC-1214 to about 30:1 and preferably from about 2:1 to about 10:1.

Of note are embodiments wherein the HF present in the first product mixture from the dehydrofluorination is not separated from CFC-1214, and CFC-1214 and HF from the dehydrofluorination is fed to fluorination reactor (e.g., as an azeotrope and/or as a non-azeotropic mixture).

The effluent from the vapor-phase fluorination reactor typically includes HCl, HF, CFC-1215yb, HCFC-225eb, $CF_3CHFCClF_2$ (HCFC-226ea), and any unreacted CFC-1214ya. If CFC-1214yb is fed to the reactor, the effluent typically includes CFC-1215yc, HCFC-225ea, and any unreacted CFC-1214yb.

The CFC-1215yb and CFC-1215yc may be separated from the product mixture by methods known to the art. Since HF is present in the effluent, if desired, this separation can also include isolation of an azeotrope or near azeotrope composition of CFC-1215yb and HF. If CFC-1215yc is present in the reactor effluent, this separation, if desired, can also include isolation of an azeotrope or near azeotrope composition of a mixture of CFC-1215yb and CFC-1215yc and HF and further processing to produce an HF-free CFC-1215yb/CFC-1215yc mixture by using procedures similar to that disclosed in U.S. Patent Application Publication No. 2006/0106263, which is incorporated herein by reference. Unreacted CFC-1214ya, optionally present as the HF azeotrope, may be recycled back to the vapor-phase fluorination reactor. Any unreacted CFC-1214 (that is CFC-1214ya and CFC-1214yb), alone or combined as the HF azeotrope may be recycled back to the vapor-phase fluorination reactor.

Of note are embodiments wherein the ratio of CFC-1215yb and CFC-1215yc, present in the CFC-1215 mixture forming an azeotrope or near azeotrope with HF vary, depending on the ratio of HCFC-225ca and HCFC-225cb present in the dehydrofluorination reactor.

In the third step of the process of this invention, the E- and/or Z—CFC-1215yb, and CFC-1215yc (if CFC-1214yb is fluorinated in the second step of the process), is contacted with $H_2$ in the presence of a catalyst comprising a catalytically effective amount of palladium supported on a support selected from the group consisting of chromium oxide, fluorinated chromium oxide, chromium fluoride, aluminum oxide, aluminum fluoride, fluorinated alumina, and mixtures thereof, for a time sufficient to convert at least a portion of CFC-1215yb to HFC-1225ye, and if CFC-1215yc is present, at least a portion of CFC-1215yc to HFC-1225yc.

The palladium-containing catalysts suitable for the hydrogenation may optionally comprise Group VIII metals (e.g., Pt, Ru, Rh or Ni). The supported metal catalysts may be prepared by conventional methods known in the art such as by impregnation of the carrier with a soluble salt of the catalytic metal (e.g., palladium chloride or rhodium nitrate) as described by Satterfield on page 95 of Heterogenous Catalysis in Industrial Practice, 2$^{nd}$ edition (McGraw-Hill, New York, 1991). The palladium-containing precursor used to prepare the catalyst is preferably a palladium salt (e.g., palladium chloride). Other metals, when used, may be added to the support during the preparation of the catalyst. Palladium supported on alumina is available commercially. Another suitable procedure for preparing a catalyst containing palladium on fluorided alumina is described in U.S. Pat. No. 4,873,381, which is incorporated herein by reference.

A catalytically effective amount of catalyst is the concentration of catalyst(s) on the support that is sufficient to carry out the catalytic reaction. For example, the concentration of palladium on the support is typically in the range of from about 0.1% to about 10% by weight based on the total weight of the catalyst and is preferably in the range of about 0.1% to about 5% by weight based on the total weight of the catalyst. The concentration of the additional Group VIII metal, when used, is about 3% by weight, or less, based on the total weight of the catalyst; but palladium is ordinarily at least 50% by weight based on the weight of the total metals present on the support, and preferably at least 80% by weight based on the weight of the total metals present on the support.

The relative amount of hydrogen fed during contact of $C_3ClF_5$ in a reaction zone containing the palladium-containing catalyst is from about 1 mole of $H_2$ per mole of $C_3ClF_5$ to about 5 moles of $H_2$ per mole of $C_3ClF_5$, preferably from about 1 mole of $H_2$ per mole of $C_3ClF_5$ to about 4 moles of $H_2$ per mole of $C_3ClF_5$ and more preferably from about 1 mole of $H_2$ per mole of $C_3ClF_5$ to about 2 moles $H_2$ per mole of $C_3ClF_5$.

The reaction zone temperature for the catalytic hydrogenation of $C_3ClF_5$ is typically in the range of from about 100° C. to about 400° C., and preferably is in the range of from about 125° C. to about 350° C. The contact time is typically in the range of from about 1 to about 450 seconds, and preferably is in the range of from about 10 to about 120 seconds. The reactions are typically conducted at near atmospheric pressure.

Of note are embodiments wherein the $C_3ClF_5$ component (that is, the total of CFC-1215yb and CFC-1215yc) subjected to contact with $H_2$ in the presence of a catalyst is primarily CFC-1215yb. Of particular note are embodiments wherein the $C_3ClF_5$ subjected to contact with $H_2$ in the presence of a catalyst is essentially free of CFC-1215yc.

Also of note are embodiments wherein the $C_3ClF_5$ component, subjected to contact with hydrogen in the presence of a catalyst, is present as an azeotrope with HF.

The effluent from the hydrogenation reaction zone typically includes HCl, unreacted hydrogen, HFC-1225ye, and one or more compounds selected from $CF_3CHFCHClF$ (HCFC-235ea), $CF_3CHFCHF_2$ (HCFC-236ea), $CF_3CHFCH_2F$ (HFC-245eb), $CF_3CF=CH_2$ (HFC-1234yf), and any unreacted CFC-1215yb. If CFC-1215yc is fed to the reactor, the effluent typically also includes HFC-1225yc, $CClF_2CHFCHF_2$ (HCFC-235eb), and any unreacted CFC-1215yc. In embodiments wherein the $C_3ClF_5$ component, subjected to contact with hydrogen in the presence of a catalyst is present as an azeotrope with HF, the effluent from the reaction zone also includes HF.

The desired HFC-1225ye, and mixtures thereof with HFC-1225yc, from the reactor effluent is separated by methods known in the art. The unreacted $C_3ClF_5$ component may be recycled back to the hydrogenation reactor. Optionally, a portion of HFC-1225ye can be separated from mixtures of HFC-1225ye and HFC-1225yc by known methods such as distillation.

In embodiments wherein HF is present in the effluent, if desired, this separation can also include isolation of an azeotrope or near azeotrope composition of HFC-1225ye and HF and HFC-1225yc and HF (if CFC-1215yc is present as part of the $C_3ClF_5$ component) and further processing to produce HF-free HFC-1225ye and HF-free HFC-1225yc by using procedures similar to that disclosed in U.S. Patent Application No. 2006/0106263, which is incorporated herein by reference.

It is noted that any CFC-1214yb in the product of step (i) need not be forwarded to step (ii); that any CFC-1215yc in the product of step (ii) need not be forwarded to step (iii); and that any HFC-1225yc formed in step (iii) need not be recovered. Accordingly, a process is provided for making $CF_3CF\!=\!CHF$, comprising (i) contacting $CHCl_2CF_2CF_3$, and optionally $CHClFCF_2CClF_2$, in a reaction zone in the presence of a catalytically effective amount of dehydrofluorination catalyst to produce $CCl_2\!=\!CFCF_3$, and, if $CHClFCF_2CClF_2$ is present, $CClF\!=\!CFCClF_2$; (ii) contacting $CCl_2\!=\!CFCF_3$ and optionally $CClF\!=\!CFCClF_2$, if any, formed in (i) with hydrogen fluoride (HF) in a reaction zone, optionally in the presence of a fluorination catalyst, to produce $CClF\!=\!CFCF_3$, and if $CClF\!=\!CFCClF_2$ is present, $CF_2\!=\!CFCClF_2$; (iii) contacting $CClF\!=\!CFCF_3$ and optionally $CF_2\!=\!CFCClF_2$, if any, formed in (ii) in a reaction zone with $H_2$ in the presence of a catalyst comprising a catalytically effective amount of palladium supported on a support selected from the group consisting of chromium oxide, fluorinated chromium oxide, chromium fluoride, aluminum oxide, aluminum fluoride, fluorinated alumina, and mixtures thereof to produce a product mixture comprising $CF_3CF\!=\!CHF$; and (iv) recovering $CF_3CF\!=\!CHF$ from the product mixture formed in (iii).

HFC-1225ye can be used for the production of HFC-1234yf. Of note is a process for production of HFC-1234yf using HFC-1225ye characterized by said HFC-1225ye being produced by the method disclosed herein. HFC-1234yf may be produced from the HFC-1225ye by adding hydrogen and $CF_3CF\!=\!CHF$ to a reaction vessel containing a hydrogenation catalyst; reacting said $CF_3CF\!=\!CHF$ with hydrogen over said hydrogenation catalyst to produce $CF_3CHFCH_2F$; and dehydrofluorinating $CF_3CHFCH_2F$ in the vapor phase over a dehydrofluorination catalyst. Suitable dehydrofluorination catalysts are selected from the group consisting of aluminum fluoride; gamma alumina, fluorided alumina; metals on aluminum fluoride; metals on fluorided alumina; oxides; fluorides, and oxyfluorides of magnesium, zinc and mixtures of magnesium and zinc and/or aluminum; lanthanum oxide and fluorided lanthanum oxide; chromium oxides, fluorided chromium oxides, cobalt-substituted chromium oxides, and cubic chromium trifluoride; carbon, acid-washed carbon, activated carbon, three dimensional matrix carbonaceous materials; and metal compounds supported on carbon, to produce $CF_3CF\!=\!CH_2$. Further details regarding the production of HFC-1234yf from HFC-1225ye are provided in International Application No. PCT/US2007/19315, which is hereby incorporated herein by reference.

The consideration of processes for the separation of individual products by distillation from the various product mixtures obtained from the different reaction steps of the processes of this invention includes the azeotropic combinations of the individual products thereof with HF.

As recognized in the art, an azeotropic composition is a constant boiling or substantially constant boiling liquid admixture of two or more different substances, wherein the admixture distills without substantial composition change and behaves as a constant boiling composition. Accordingly, the essential features of an azeotropic composition are that at a given pressure, the boiling point of the liquid composition is fixed and that the composition of the vapor above the boiling composition is essentially that of the boiling liquid composition (i.e., no substantial fractionation of the components of the liquid composition takes place). It is also recognized in the art that both the boiling point and the weight percentages of each component of the azeotropic composition may change when the azeotrope composition is subjected to boiling at different pressures. Thus, an azeotropic composition may be defined in terms of the unique relationship that exists among the components or in terms of the compositional ranges of the components or in terms of the weight percentages of each component of the composition characterized by a fixed boiling point at a specified pressure. It is also recognized in the art that various azeotropic compositions (including their boiling points at particular pressures) may be calculated (see, e.g., W. Schotte Ind. Eng. Chem. Process Des. Dev. (1980) 19, 432-439). Experimental identification of azeotropic compositions involving the same components may be used to confirm the accuracy of such calculations and/or to modify the calculations at the same temperature and pressure or at other temperatures and pressures.

As noted above, the present invention provides azeotropic compositions comprising hydrogen fluoride combined with CFC-1214ya. In accordance with this invention, compositions are provided which comprise the CFC-1214ya and HF, wherein the HF is present in an effective amount to form an azeotropic combination with the CFC-1214ya. According to calculations, these compositions include embodiments comprising from about 95 mole percent to about 76 mole percent HF and from about 5 mole percent to about 24 mole percent CFC-1214ya (which form azeotropes boiling at temperatures between about −25° C. and about 125° C. and at pressures between about 2 psia (13.8 kPa) and about 372 psia (2565 kPa)). Compositions may be formed that consist essentially of azeotrope combinations of hydrogen fluoride with CFC-1214ya. These include compositions calculated to consist essentially of from about 95 mole percent to about 76 mole percent HF and from about 5 mole percent to about 24 mole percent CFC-1214ya (which forms an azeotrope boiling at temperatures between about −25° C. and about 125° C. and at pressures of between about 2 psia (13.8 kPa) and about 372 psia (2565 kPa)). Azeotropic compositions of HF and CFC-1214ya are useful as sources of HF in fluorination reactions. For example by combining the azeotrope of HF and CFC-1214ya with fluorination precursor compounds it is possible to obtain HF-free CFC-1214ya and a fluorinated product (see for example, U.S. Pat. No. 6,224,781).

As noted above, the present invention also provides azeotropic compositions comprising hydrogen fluoride combined with a mixture of CFC-1214ya and CFC-1214yb. In accordance with this invention, compositions are provided which comprise CFC-1214ya, CFC-1214yb and HF, wherein the HF is present in an effective amount to form an azeotropic combination with the CFC-1214ya and CFC-1214yb. According to calculations, these compositions include embodiments comprising from about 95 mole percent to about 76 mole percent HF and from about 5 mole percent to about 24 mole percent total CFC-1214ya and CFC-1214yb (which form azeotropes boiling at temperatures between about −25° C. and about 125° C. and at pressures between about 2 psia (13.8 kPa) and 372 psia (2565 kPa)). Compositions may be formed that consist essentially of azeotropic combinations of hydrogen fluoride with CFC-1214ya and CFC-1214yb. These include compositions calculated to consist essentially of from about 95 mole percent to about 76 mole percent HF and from about 5 mole percent to about 24 mole percent total CFC-1214ya and CFC-1214yb (which form azeotropes boiling at temperatures between about −25° C. and about 125° C. and at pressures between about 2 psia (13.8 kPa) and about 372 psia (2565 kPa)).

Azeotropic compositions of HF, CFC-1214ya and CFC-1214yb are useful as sources of HF in fluorination reactions. For example by combining the azeotrope of HF, CFC-1214ya and CFC-1214yb with fluorination precursor compounds it is possible to obtain HF-free CFC-1214ya and CFC-1214yb and a fluorinated product (see for example, U.S. Pat. No. 6,224,781).

As noted above, the present invention also provides azeotropic compositions comprising hydrogen fluoride combined with CFC-1215yb. In accordance with this invention, compositions are provided which comprise CFC-1215yb and HF, wherein the HF is present in an effective amount to form an azeotropic combination with the CFC-1215yb. According to calculations, these compositions include embodiments comprising from about 75 mole percent to about 55 mole percent HF and from about 25 mole percent to about 45 mole percent CFC-1215yb (which form azeotropes boiling at temperatures between about −25° C. and about 100° C. and at pressures between about 4 psia (27.6 kPa) and about 400 psia (2760 kPa)). Compositions may be formed that consist essentially of azeotropic combinations of hydrogen fluoride with CFC-1215yb. These include compositions calculated to consist essentially of from about 75 mole percent to about 55 mole percent HF and from about 25 mole percent to about 45 mole percent CFC-1215yb (which form azeotropes boiling at temperatures between about −25° C. and about 100° C. and at pressures between about 4 psia (27.6 kPa) and about 400 psia (2760 kPa)).

Subsequent to these calculations, it has been confirmed based on experiments that azeotropes of CFC-1215yb and HF are formed at a variety of temperatures and pressures. For example, an azeotrope of HF and CFC-1215yb at 29.80° C. and 52.2 psi (359.9 kPa) has been found to consist essentially of about 64.7 mole percent HF and about 35.3 mole percent CFC-1215yb. An azeotrope of HF and CFC-1215yb at 74.55° C. and 188.8 psi (1302 kPa) has been calculated to consist essentially of about 60.3 mole percent HF and about 39.7 mole percent CFC-1215yb.

According to calculations based on the experiments, azeotropic compositions are provided that comprise from about 73.5 mole percent to about 57.6 mole percent HF and from about 26.5 mole percent to about 42.4 mole percent CFC-1215yb (which form azeotropes boiling at a temperature of from between about −40° C. and about 110° C. and at a pressure of from between about 2.36 psi (16.3 kPa) and about 442 psi (3047 kPa)). Also provided are compositions consisting essentially of from about 73.5 mole percent to about 57.6 mole percent HF and from about 26.5 mole percent to about 42.4 mole percent CFC-1215yb (which forms an azeotrope boiling at a temperature from between about −40° C. and about 110° C. and at a pressure of from between about 2.36 psi (16.3 kPa) and about 442 psi (3047 kPa)).

Azeotropic compositions of HF and CFC-1215yb are useful as sources of HF in fluorination reactions. For example by combining the azeotrope of HF and CFC-1215yb with fluorination precursor compounds it is possible to obtain HF-free CFC-1215yb and a fluorinated product (see for example, U.S. Pat. No. 6,224,781).

As noted above, the present invention also provides azeotropic compositions comprising hydrogen fluoride combined with a mixture of CFC-1215yb and CFC-1215yc. In accordance with this invention, compositions are provided which comprise CFC-1215yb, CFC-1215yc and HF, wherein the HF is present in an effective amount to form an azeotropic combination with CFC-1215yb and CFC-1215yc. According to calculations, these compositions include embodiments comprising from about 71 mole percent to about 56 mole percent HF and from about 29 mole percent to about 44 mole percent total CFC-1215yb and CFC-1215yc (which form azeotropes boiling at temperatures between about −25° C. and about 100° C. and at pressures between about 5 psia (34.5 kPa) and about 400 psia (2760 kPa)). Compositions may be formed that consist essentially of azeotropic combinations of hydrogen fluoride with CFC-1215yb and CFC-1215yc. These include compositions calculated to consist essentially of from about 71 mole percent to about 56 mole percent HF and from about 29 mole percent to about 44 mole percent total CFC-1215yb and CFC-1215yc (which form azeotropes boiling at temperatures between about −25° C. and about 100° C. and at pressures between about 5 psia (34.5 kPa) and about 400 psia (2760 kPa)). Azeotropic compositions of HF, CFC-1215yb and CFC-1215yc are useful as sources of HF in fluorination reactions. For example by combining the azeotrope of HF, CFC-1215yb and CFC-1215yc with fluorination precursor compounds it is possible to obtain HF-free CFC-1215yb and CFC-1215yc and a fluorinated product (see for example, U.S. Pat. No. 6,224,781).

As noted above, the present invention also provides azeotrope compositions comprising hydrogen fluoride combined with HFC-1225yc. In accordance with this invention, compositions are provided which comprise HFC-1225yc and HF, wherein the HF is present in an effective amount to form an azeotropic combination with the HFC-1225yc. According to calculations, these compositions include embodiments comprising from about 58 mole percent to about 54 mole percent HF and from about 42 mole percent to about 46 mole percent HFC-1225ye (which form azeotropes boiling at temperatures between about −25° C. and about 125° C. and at pressures between about 6 psia (41.4 kPa) and about 450 psia (3100 kPa)). Compositions may be formed that consist essentially of azeotrope combinations of hydrogen fluoride with HFC-1225yc. These include compositions calculated to consist essentially of from about 58 mole percent to about 54 mole percent HF and from about 42 mole percent to about 46 mole percent HFC-1225yc (which forms azeotropes boiling at temperatures between about −25° C. and about 125° C. and at pressures between about 6 psia (41.4 kPa) and 450 psia (3100 kPa)).

Subsequent to these calculations, it has been confirmed based on experiments that azeotropes of HFC-1225yc and HF are formed at a variety of temperatures and pressures. For example, an azeotrope of HF and HFC-1225yc at 29.81° C. and 55.2 psi (380.5 kPa) has been found to consist essentially of about 49.9 mole percent HF and about 50.1 mole percent HFC-1225yc.

According to calculations based on the experiments, azeotropic compositions are provided that comprise from about 68.6 mole percent to about 42.8 mole percent HF and from about 31.4 mole percent to about 57.2 mole percent HFC- 1225yc (which form azeotropes boiling at a temperature of from between about −40° C. and about 90° C. and at a pressure of from between about 2.32 psi (16.0 kPa) and about 474 psi (3268 kPa)). Also provided are compositions consisting essentially of from about 68.6 mole percent to about 42.8 mole percent HF and from about 31.4 mole percent to about 57.2 mole percent HFC-1225yc (which forms an azeotrope boiling at a temperature from between about −40° C. and about 90° C. and at a pressure of from between about 2.32 psi (16.0 kPa) and about 474 psi (3268 kPa)).

Azeotropic compositions of HF and HFC-1225yc are useful as sources of HF in fluorination reactions. For example by combining the azeotrope of HF and HFC-1225yc with fluorination precursor compounds it is possible to obtain HF-free HFC-1225yc and a fluorinated product (see for example, U.S. Pat. No. 6,224,781).

The reactor, distillation columns, and their associated feed lines, effluent lines, and associated units used in applying the process of this invention should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

EXAMPLES

The processes of the present invention are demonstrated by the following prophetic examples.

Example 1

Dehydrofluorination of HCFC-225ca ($CHCl_2C_2F_5$) and HCFC-225cb ($CHClFCF_2CClF_2$)

An Inconel™ tube (⅝ inch OD (1.59 cm)) is charged with a commercial sample of 25 weight percent chromium(III) chloride supported on carbon (10 cc, 3.4 g, 12-20 mesh (1.68-0.84 mm)). The tube is connected to a reactor system and surrounded with an electrically-heated furnace. The catalyst is then activated by purging with nitrogen (37.5 sccm, 6.2×10$^{-7}$ m$^3$/s) at 300° C. for 2 hours. The catalyst is then fluorinated with a 3:1 mixture of nitrogen and hydrogen fluoride (total flow 35 sccm, 5.8×10$^{-7}$ m$^3$/s) as the temperature in the reactor is increased from 300° C. to 425° C. over the course of 9 hours. The ratio of nitrogen to hydrogen fluoride is then changed from 3:1 to 0:4 with a total flow rate of 35 sccm (5.8×10$^{-7}$ m$^3$/s) over the course of 3 hours at 425° C. The flow of HF is then stopped and the reactor cooled to about 350° C. under a nitrogen flow.

A mixture of HCFC-225ca (41%) and HCFC-225cb (59%) and nitrogen (molar ratio 1:3) is then passed through the catalyst bed at 350° C. with a contact time of about 30 seconds. The pressure in the reactor is nominally atmospheric. Analysis of the reactor effluent shows at least 50% or the HCFC-225ca component is converted with CFC-1214ya being the major reaction product. The effluent also contains unreacted starting materials and lesser amounts of CFC-1214yb and $C_3HCl_3F_4$ and $C_3HClF_6$ isomers.

Example 2

Fluorination of a CFC-1214ya ($CF_3CF=CCl_2$)/ CFC-1214yb (E/Z—$CClF_2CF=CClF$) Mixture A metal oxide fluorination catalyst comprising 95 atom % chromium and 5 atom % zinc is prepared by co-precipitation of a mixture of chromium and zinc hydroxides as disclosed in U.S. Pat. No. 7,285,691. The mixture is dried and calcined at 900° C.

The calcined catalyst is pelletized (12-20 mesh (1.68-0.84 mm)) and 14 g (10 cc) of the solid is placed in a 30.5 cm×1.27 cm o.d. Hastelloy® tube. The tube is connected to a reactor system and is surrounded with an electrically-heated furnace. The tube is heated from 50° C. to 175° C. in a flow of nitrogen (50 cc/min; 8.3(10)$^{-7}$ m$^3$/sec) over the course of about one hour. HF is then admitted to the reactor at a flow rate of 50 cc/min (8.3(10)$^{-7}$ m$^3$/sec). After 2 hours, the nitrogen flow is decreased to 20 cc/min (3.3(10)$^{-7}$ m$^3$/sec) and the HF flow is increased to 80 cc/min (1.3(10)$^{-6}$ m$^3$/sec); this flow is maintained for about 1 hour. The reactor temperature is then gradually increased to 400° C. over 5 hours. At the end of this period, the HF flow is stopped and the reactor cooled to 300° C. under 20 sccm (3.3(10)$^{-7}$ m$^3$/sec) nitrogen flow.

A mixture of hydrogen fluoride and CFC-1214ya/E/Z—CFC-1214yb is then fed to the catalyst at 300° C. with a contact time of 30 seconds; the overall molar ratio of HF to $C_3Cl_2F_4$ is 8:1 and the molar ratio of CFC-1214ya to CFC-1214yb is 20:1. The pressure in the reactor is nominally atmospheric. Under these conditions, at least 50% of the CFC-1214ya is converted with E/Z—$CF_3CF=CClF$ being the major reaction product. The effluent also contains unreacted starting materials and lesser amounts of $CClF_2CF=CF_2$ and $C_3HCl_2F_5$ isomers.

Example 3

Hydrodechlorination of CFC-1215yb ($CF_3CF=CClF$)

A commercial palladium on aluminum oxide catalyst (0.5% Pd/Al$_2$O$_3$, 10 cc, 14.45 g, 12-20 mesh (1.68-0.84 mm)) is placed in a 30.5 cm×1.27 cm o.d. Hastelloy® tube. The tube is connected to a reactor system and surrounded with an electrically-heated furnace. The catalyst is dried for three hours under a nitrogen purge (25 sccm, 4.2×10$^{-7}$ m$^3$/s) as the temperature of the furnace is raised to 300° C. The reactor is allowed to cool to 150° C. and then hydrogen gas (20 sccm, 3.3×10$^{-7}$ m$^3$/s) is passed into the reactor for three hours as the temperature in the reactor is increased to 300° C. The reactor is cooled again to 150° C. under a flow of nitrogen (20 sccm, 3.3×10$^{-7}$ m$^3$/s). The catalyst is then fluorinated with mixture of nitrogen and hydrogen fluoride according to following sequence (time in hours, flow rate nitrogen, flow rate HF, temperature):
2 h, 7.5×10$^{-7}$ m$^3$/s, 8.3×10$^{-8}$ m$^3$/s, 150° C.; 2 h, 6.6×10$^{-7}$ m$^3$/s, 1.7×10$^{-7}$ m$^3$/s, 150° C.; 2 h, 6.6×10$^{-7}$ m$^3$/s, 1.7×10$^{-7}$ m$^3$/s, 200° C.; 2 h, 6.6×10$^{-7}$ m$^3$/s, 1.7×10$^{-7}$ m$^3$/s, 250° C.; 2 h, 4.2×10$^{-7}$ m$^3$/s, 4.2×10$^{-7}$ m$^3$/s, 250° C. The flow of hydrogen fluoride is then stopped and the reactor is purged with nitrogen.

A mixture of hydrogen, $CF_3CF=CClF$ (CFC-1215yb, an E/Z mixture), and nitrogen in a 1:1:2 molar ratio is then fed to the catalyst at 200° C. with a contact time of 30 seconds. The pressure in the reactor is nominally atmospheric. Under these conditions, at least 50% of the CFC-1215yb is converted with E/Z—$CF_3CF=CHF$ being the major reaction product. The effluent also contains unreacted starting materials and lesser amounts of $CF_3CHFCH_2F$ and $CF_3CF=CH_2$.

What is claimed is:

1. A process for making $CF_3CF=CHF$, comprising:
   i. contacting $CHCl_2CF_2CF_3$, in a reaction zone in the presence of a catalytically effective amount of dehydrofluorination catalyst to produce $CCl_2=CFCF_3$;

ii. contacting $CCl_2=CFCF_3$ formed in (i) with hydrogen fluoride (HF) in a reaction zone, optionally in the presence of a fluorination catalyst, to produce $CClF=CFCF_3$;

iii. contacting $CClF=CFCF_3$ formed in (ii) in a reaction zone with $H_2$ in the presence of a catalyst comprising a catalytically effective amount of palladium supported on a support selected from the group consisting of chromium oxide, fluorinated chromium oxide, chromium fluoride, aluminum oxide, aluminum fluoride, fluorinated alumina, and mixtures thereof to produce a product mixture comprising $CF_3CF=CHF$; and iv. recovering $CF_3CF=CHF$ from the product mixture formed in (iii).

2. The process of claim 1 wherein the $C_3HCl_2F_5$ dehydrofluorinated in (i) is produced by reacting $CHCl_2F$ with $CF_2=CF_2$ in a reaction zone in the presence of a catalytically effective amount of an aluminum halide composition having a bulk formula of $AlCl_xBr_yF_{3-x-y}$ wherein the average value of x is 0 to 3, the average value of y is 0 to 3-x, provided that the average values of x and y are not both 0.

3. The process of claim 1 wherein the $C_3HCl_2F_5$ dehydrofluorinated in (i) is essentially free of $CHClFCF_2CClF_2$.

4. The process of claim 1 wherein the $C_3Cl_2F_4$ fluorinated in (ii) is essentially free of $CClF=CFCClF_2$.

5. A process for producing HFC-1234yf using HFC-1225ye, characterized by making said HFC-1225ye by the process of claim 1.

6. The process of claim 5 comprising the steps of a) adding hydrogen and $CF_3CF=CHF$ to a reaction vessel containing a hydrogenation catalyst;

b) reacting said $CF_3CF=CHF$ with hydrogen over said hydrogenation catalyst to produce $CF_3CHFCH_2F$; and c) dehydrofluorinating $CF_3CHFCH_2F$ in the vapor phase over a dehydrofluorination catalyst.

7. The process of claim 1, further comprising:

i. contacting $CHCl_2CF_2CF_3$ and $CHClFCF_2CClF_2$, in a reaction zone in the presence of a catalytically effective amount of dehydrofluorination catalyst to produce $CCl_2=CFCF_3$, and $CClF=CFCClF_2$;

ii. contacting $CCl_2=CFCF_3$ and $CClF=CFCClF_2$, formed in (i) with hydrogen fluoride (HF) in a reaction zone, optionally in the presence of a fluorination catalyst, to produce $CClF=CFCF_3$ and $CF_2=CFCClF_2$;

iii. contacting $CClF=CFCF_3$ and $CF_2=CFCClF_2$, formed in (ii) in a reaction zone with $H_2$ in the presence of a catalyst comprising a catalytically effective amount of palladium supported on a support selected from the group consisting of chromium oxide, fluorinated chromium oxide, chromium fluoride, aluminum oxide, aluminum fluoride, fluorinated alumina, and mixtures thereof to produce a product mixture comprising $CF_3CF=CHF$; and iv. recovering $CF_3CF=CHF$ from the product mixture formed in (iii).

8. An azeotropic composition comprising (a) from about 5 mole percent to about 24 mole percent $CCl_2=CFCF_3$ and (b) from about 76 mole percent to about 95 mole percent HF, having a vapor pressure of from about 2 psia to about 372 psia, at a temperature of from about −25° C. to about 125° C.

9. An azeotropic composition comprising (a) from about 5 mole percent to about 24 mole percent of a mixture of $CCl_2=CFCF_3$ and $CClF=CFCClF_2$ and (b) from about 76 mole percent to about 95 mole percent HF, having a vapor pressure of from about 2 psia to about 372 psia, at a temperature of from about −25° C. to about 125° C.

10. An azeotropic composition comprising (a) from about 25 mole percent to about 45 mole percent $CClF=CFCF_3$ and (b) from about 55 mole percent to about 75 mole percent HF, having a vapor pressure of from about 4 psia to about 400 psia at a temperature of from about −25° C. to about 100° C.

11. An azeotropic composition comprising (a) from about 29 mole to about 44 mole percent of a mixture of $CClF=CFCF_3$ and $CF_2=CFCClF_2$ and (b) from about 56 mole percent to about 71 mole percent HF, having a vapor pressure of from about 5 psia to about 400 psia, at a temperature of from about −25° C. to about 100° C.

12. An azeotropic composition comprising (a) from about 42 mole percent to about 46 mole percent $CF_2=CFCHF_2$ and (b) from about 54 mole percent to about 58 mole percent HF, having a vapor pressure of from about 6 psia to about 450 psia, at a temperature of from about −25° C. to about 125° C.

* * * * *